United States Patent [19]

Demers

[11] Patent Number: 5,685,084
[45] Date of Patent: Nov. 11, 1997

[54] DENTAL MEASURING APPARATUS

[76] Inventor: Jag L. Demers, 5850 Bannantyne, Verdun, Quebec, Canada, H4H 1H3

[21] Appl. No.: 582,558

[22] Filed: Jan. 2, 1996

Related U.S. Application Data

[63] Continuation-in-part of Ser. No. 282,366, Jul. 29, 1994, abandoned.

[51] Int. Cl.$^6$ .................................................. A16C 19/04
[52] U.S. Cl. .............................. 33/513; 433/72; 33/812
[58] Field of Search .............................. 33/511, 512, 513, 33/514, 783, 794, 806, 809, 832, 833, 419, 427, 452, 464; 433/25, 72

[56] References Cited

U.S. PATENT DOCUMENTS

| | | | |
|---|---|---|---|
| 636,098 | 10/1899 | Arnot | 33/783 |
| 696,120 | 3/1902 | Vanderpool | 33/513 |
| 1,393,746 | 10/1921 | Bushnell | 33/783 |
| 1,649,664 | 11/1927 | Carter | 433/25 |
| 1,901,724 | 3/1933 | Bennett | 433/72 |
| 1,907,923 | 5/1933 | Willis | 433/25 |
| 1,944,601 | 1/1934 | Gulick | 33/513 |
| 1,976,045 | 10/1934 | Sorenson | 33/513 |
| 2,107,534 | 2/1938 | Houser | 33/513 |
| 3,381,377 | 5/1968 | Grayson | 32/19 |
| 3,708,885 | 1/1973 | Christ | 33/548 |
| 3,906,634 | 9/1975 | Aspel | 433/72 |
| 4,718,850 | 1/1988 | Knebelman | 433/72 |
| 4,840,564 | 6/1989 | Segal | 433/72 |
| 4,843,720 | 7/1989 | Kim | 33/812 |

FOREIGN PATENT DOCUMENTS

| | | | |
|---|---|---|---|
| 1175344 | 5/1957 | France | 433/72 |
| 375064 | 6/1973 | U.S.S.R. | 433/72 |

*Primary Examiner*—G. Bradley Bennett
*Attorney, Agent, or Firm*—Goudreau Gage Dubuc & Martineau Walker

[57] ABSTRACT

A dental apparatus for accurately measuring dentures comprises a C-shaped body, a horizontal ruler and a vertical ruler. The rulers are graduated and movable to determine the distance of the teeth from the center of the ridge and the intermaxillary distance of the two dentures.

8 Claims, 2 Drawing Sheets

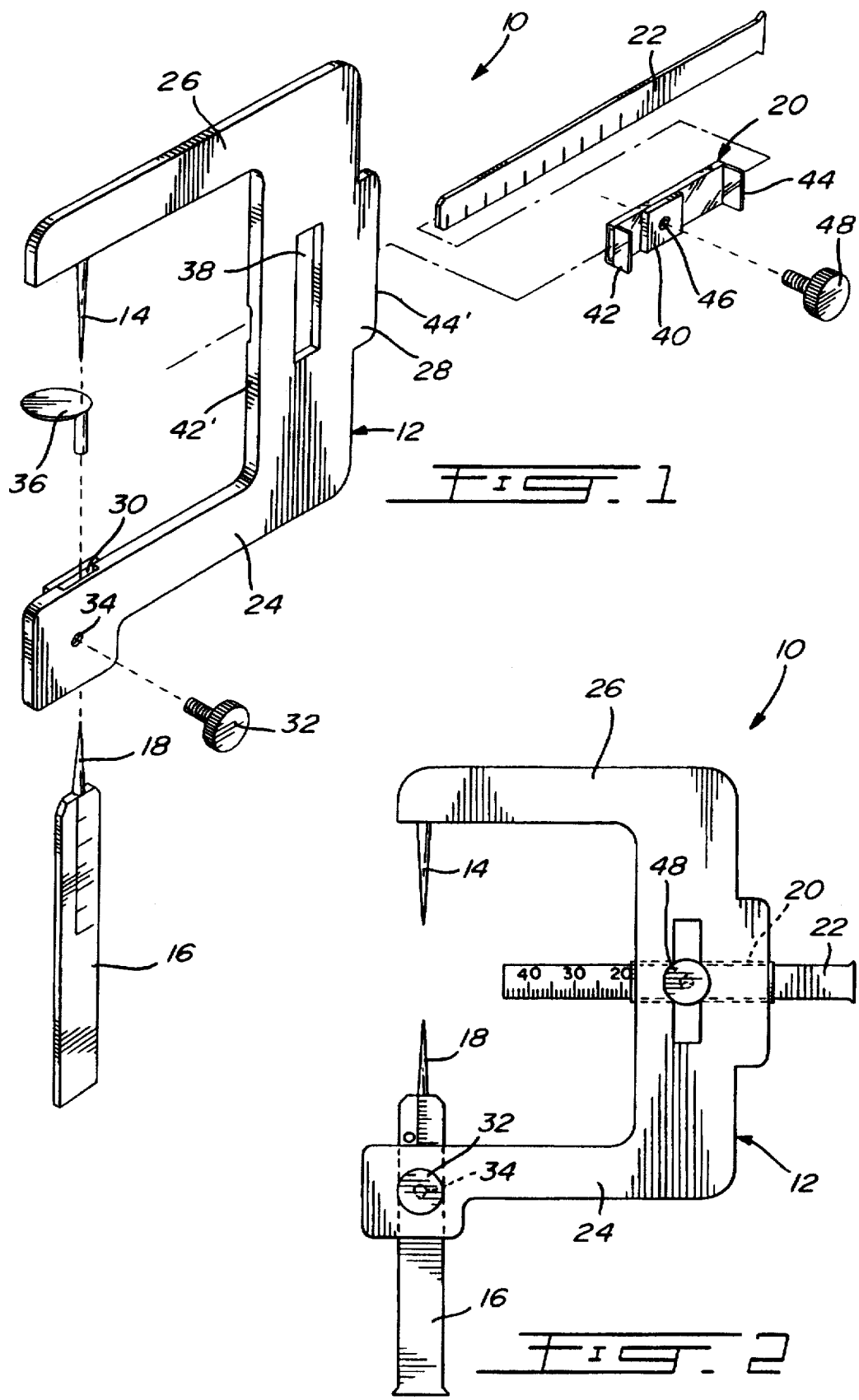

5,685,084

1

DENTAL MEASURING APPARATUS

This is a continuation-in-part of application Ser. No. 08/282,366 filed on Jul. 29, 1994 and entitled: "A measuring instrument to make an exact duplication of a set of upper and lower dentures", now abandoned.

FIELD OF THE INVENTION

The present invention relates to dentures. More specifically, the present invention relates to a dental apparatus adapted to measure existing dentures and to transfer the measures to a rim of deformable material mounted to a conventional base-plate.

BACKGROUND OF THE INVENTION

In the practice of dentistry, practitioners are routinely confronted with patients needing new dentures to replace worn or damaged dentures. Because of the aesthetic or comfort they enjoy, many patients want the new dentures to have the same dimensions as their prior dentures.

In these cases, the practitioner is faced with a problem. Indeed, denture duplicating is a procedure that can be quite difficult, since a small difference between the size of the new denture and the size of the prior denture may cause some discomfort to the patient and/or may modify the overall aesthetic appearance of the patient's mouth.

Various apparatuses have been developed in the past to help the practitioner measure the existing configuration of the patient. Many of those apparatuses are adapted to take measurements of the patient face while wearing the existing dentures or when he is wearing no dentures at all. The U.S. patents listed in the following table (Table 1) describe apparatuses of this type:

TABLE 1

| Patent N° | Inventor(s) | Issue Date |
| --- | --- | --- |
| 0,696,120 | Venderpool | 03/25/1902 |
| 1,649,664 | Carter | 11/15/1927 |
| 1,901,724 | Bennett | 03/14/1933 |
| 1,907,923 | Willis | 05/09/1933 |
| 1,944,601 | Gulick | 01/23/1934 |
| 1,976,045 | Sorenson | 10/09/1934 |
| 2,107,534 | Houser | 02/08/1938 |
| 4,718,850 | Knebelman | 01/12/1988 |
| 4,848,720 | Kim | 07/04/1989 |

The apparatuses described suffer from a common drawback, which is to lack the adequate measurement accuracy, since these apparatuses bear or contour soft and yielding tissue. Therefore, if these apparatuses are used to measure existing dentures to provide the practitionner with data to replicate these existing dentures, the measurements may be incorrect and lead the practitionner to make new dentures which are different from the existing dentures.

U.S. Pat. No. 4,840,564 issued on Jun. 20, 1989 to Segal describes a dental measuring apparatus for accurately measuring dentures, models, bite blocks and the like. This apparatus includes a table provided with a scale, a support mounted to the table, and a probe mounted to the support and provided with a scaled indicator. The apparatus enables the practitioner to take horizontal measurements by means of the scale provided on the table, and vertical measurements by means of the scaled indicator of the probe.

A drawback with the apparatus described by Segal is the relative difficulty to read the scale provided on the table since the denture is placed over the scale and the measurement must be taken at the contact between the denture and the table.

OBJECTS OF THE INVENTION

An object of the present invention is therefore to provide an improved dental apparatus for measuring existing dentures.

Another object of the invention is to provide a dental measuring apparatus which is simple to use, and which allows the transfer of a measurement from an existing denture to a rim of deformable material mounted to a conventional base-plate.

SUMMARY OF THE INVENTION

More specifically, in accordance with the present invention, there is provided a dental measuring apparatus for measuring existing dentures comprising:

- a substantially C-shaped body including a first arm, a second arm and an intermediate part defining a longitudinal axis;
- a first reference member mounted to the first arm; the first reference member projecting in a direction substantially parallel to the longitudinal axis and towards the second arm;
- first ruler means mounted to the second arm; the first ruler means being slidable in a direction substantially colinear with the first reference member;
- connecting means mounted to the intermediate part; the connecting means being slidable along the longitudinal axis; and
- second ruler means mounted to the connecting means; the second ruler means being slidable in a direction substantially perpendicular to the longitudinal axis;
- whereby, by placing the existing dentures between the first reference member and the first ruler means, measurements of an existing denture in a direction parallel to the longitudinal axis may be determined from the first ruler means and, by sliding the second ruler means towards the denture, measurements of the existing denture in a direction perpendicular to the longitudinal axis may be determined from the second ruler means.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 1 illustrates an exploded view of a dental measuring apparatus according to an embodiment of the present invention;

FIG. 2 illustrates a side elevational view of the dental measuring apparatus of FIG. 1;

DESCRIPTION OF THE PREFERRED EMBODIMENT

Figure 3:
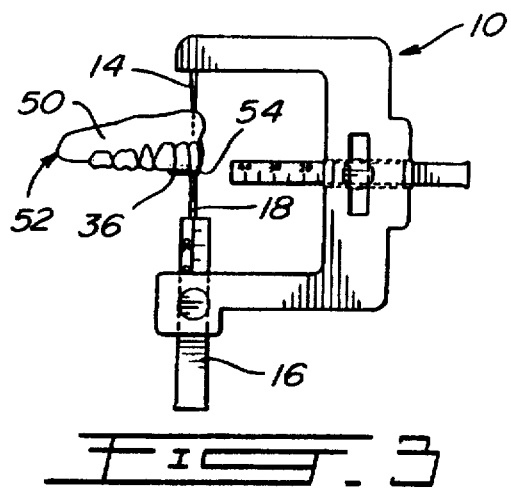
FIG. 3 illustrates a side elevational view of the dental measuring apparatus of FIG. 1 measuring an existing denture along a substantially vertical direction.

Referring now to FIGS. 1 and 2 of the appended drawings, a dental measuring apparatus 10 according to an embodiment of the present invention will be described.

The dental measuring apparatus 10 includes a C-shaped body 12 provided with a first reference point 14, a first ruler 16 provided with a second reference point 18, a sleeve connector 20 and a second ruler 22.

The C-shaped body includes a lower arm 24, an upper arm 26 and an intermediate portion 28.

The lower arm 24 includes an aperture 30 adapted to slidably receive the first ruler 16 therein. A fastener 32 is removably inserted in a threaded aperture 34 of the lower arm 24 to thereby allow the first ruler 16 to be locked at a predetermined position. Indeed, if the fastener 32 is tightened while the first ruler 16 is in the aperture 30, the frictional contact between the fastener 32 and the ruler 16 will prevent sliding movements of the ruler 16 in the aperture 30.

A plate member 36, forming a shelf and adapted to be mounted to the second reference point 18 is also illustrated in FIG. 1. The purpose of the plate member 36 will be described hereinafter.

The intermediate portion 28 of the C-shaped body 12 includes a rectangular aperture 38, and the sleeve connector 20 includes a square protrusion 40 sized to enter the rectangular aperture 38. The sleeve connector 20 also includes first and second wings 42, 44 so mounted that they respectively contact the inner edge 42' and the outer edge 44' of the intermediate portion 28 when the square protrusion 40 is inserted in the rectangular aperture 38. The sleeve connector 20 may therefore be mounted to the intermediate portion 28 so that it may longitudinally slide thereon. The intermediate portion 28 is also provided with a notch 39 dimentioned to receive the sleeve connector 20 when it is not necessary to slide longitudinally the sleeve connector 20 as will be described hereinafter.

The square protrusion 40 of the sleeve connector 20 includes a threaded aperture 46 to receive a fastener 48 and thereby allow the sleeve connector 20 to be locked to the intermediate portion 28 at a predetermined location. Indeed, if the fastener 48 is tightened when the sleeve connector 20 is mounted to the intermediate portion 28 of the body 12, the intermediate portion 28 is compressed between the sleeve connector 20 and the fastener 48 thereby preventing the sleeve connector 20 from sliding in the rectangular aperture 38.

The second ruler 22 is slidably mounted to the sleeve connector 20.

Referring to FIGS. 3–8, the operation of the dental measuring apparatus 10 will now be described.

It is to be noted that, for concision purposes, the following description of the operation of the dental measuring apparatus 10 will consider only the measurements of the upper central incisors and of the intermaxillary space, and the transfer of these measures to a rim of deformable material (usually a wax rim) mounted to a base-plate. Of course, the dental measuring apparatus 10 of the present invention could be used to take measurements of each teeth of existing dentures, and to transfer these measures to a rim of deformable material.

It is also to be noted that the size of the deformable rim is larger than the size of the existing dentures, to allow the practitioner to remove some portions of the deformable rim to obtain the exact dimensions of the existing dentures.

As will be obvious to one of ordinary skills in the art of dentistry, the following description of the operation of the dental measuring apparatus 10 will focus on the steps of denture making involving the present invention. The other steps performed by the practitioner are considered well known in the art and will therefore be omitted from the foregoing description.

The present invention, is used to measure the existing dentures and to transfer the measurements to a deformable rim mounted to a base-plate. It implies that:

the impressions of the upper and lower gums of the patient were already taken;

the impressions of the old dentures to be duplicated and the stone cast models of the old dentures were already made.

STEP 1

Measuring and Transferring the Upper Incisors Position

The first step is to measure and to transfer the upper incisors position in relation to the lowest part of the ridge of the upper maxillary at center front. To determine this position, two measurements are done: the vertical distance and the horizontal distance.

FIG. 3 illustrates the measurement of the vertical distance from the lowest part of the gum ridge 50 of the upper denture 52 to the incisors lower edge 54 with the first calibrated ruler 16. To perform this measurement, the plate member 36 is inserted on the tip of the second reference point 18. The first reference point 14 is inserted in the center front in the lowest part of the gum ridge 50. The first ruler 16 is pushed upwards until the plate member 36 meets the lower edge 54 of the incisors. The practitioner may then read the vertical distance between the first reference point 14 and the plate member 36 on the first calibrated ruler 16 and write this measure down on the patient's chart.

Figure 4:
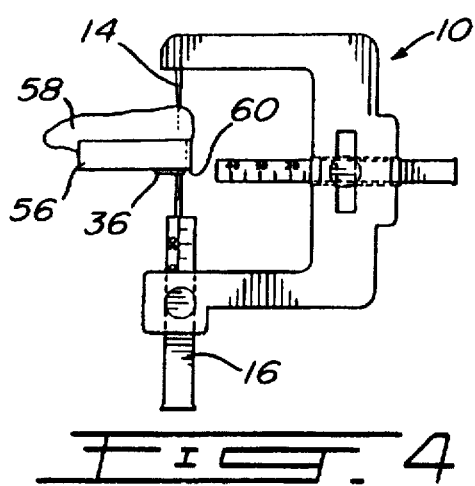
FIG. 4 illustrates a side elevational view of the dental measuring apparatus of FIG. 1 transferring measurements of an existing denture along a substantially vertical direction to a rim of deformable material mounted to a base-plate.

FIG. 4 illustrates the transfer of the vertical distance measurement to a deformable rim 56 mounted to a base-plate 58. The practitioner places the base-plate 58 so that the first reference point 14 is inserted in the center front of the lowest part of the base-plate 58. The distance from the lowest part of the inside of the base-plate 58 to the lower edge 60 of the deformable rim 56 may then be measured with the first calibrated ruler 16 as previously described. The practitioner then determines the quantity of material in excess from the deformable rim 56 by performing a substraction and trims this material in excess so as to obtain a vertical distance identical to the vertical distance measured on the existing denture.

Figure 5:
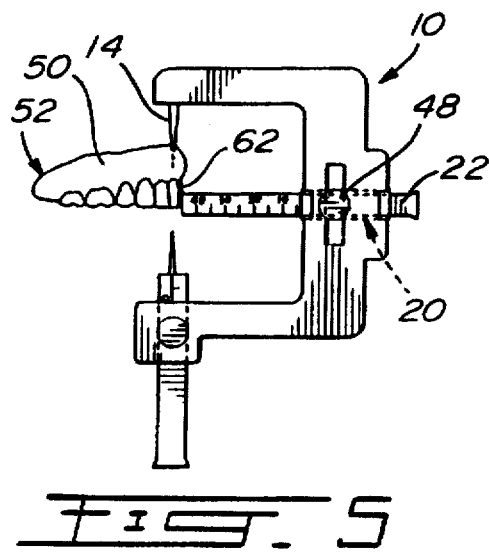
FIG. 5 illustrates a side elevational view of the dental measuring apparatus of FIG. 1 measuring an existing denture along a substantially horizontal direction.

FIG. 5 illustrates the measurement of the horizontal distance from the bottom of the gum ridge 50 of the upper denture 52 to the incisors vertical edge 62 with the second calibrated ruler 22. The first reference point 14 is inserted in the center front of the lowest part of the gum ridge 50 of the denture 52. The second calibrated ruler 22 is pushed towards the central incisors vertical edge 62. The practitioner may then read the vertical distance indicated on the ruler 22 and write it down on the patient's chart.

It is to be noted that the sleeve connector 20 may be vertically displaced, if necessary, to allow the second calibrated ruler 22 to touch the central incisors vertical edge 62. If this is the case, the fastener 48 is tightened so as to lock the sleeve connector 20 in position for the transfer of the measurement to the rim of deformable material as will be described hereinbelow.

Figure 6:
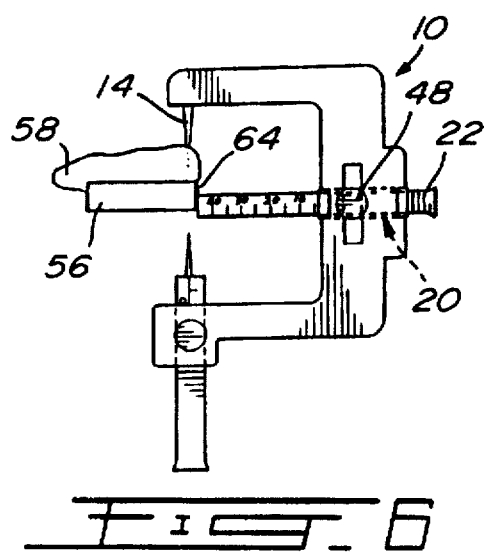
FIG. 6 illustrates a side elevational view of the dental measuring apparatus of FIG. 1 transferring measurements of an existing denture along a substantially horizontal direction to a rim of deformable material mounted to a base-plate.

FIG. 6 illustrates the transfer of the horizontal distance to the deformable rim 56 mounted to the base-plate 58. The practitioner places the base-plate 58 so that the first reference point 14 is inserted in the center front of the lowest part of the base-plate 58. The horizontal distance from the lowest part of the inside of the base-plate 58 to the vertical edge 64 of the deformable rim 56 may then be measured with the second calibrated ruler 22 as previously described. The practitioner then determines the quantity of material in excess from the deformable rim 56 by performing a substraction and trims this material in excess so as to obtain a horizontal distance identical to the horizontal distance measured on the existing denture. The deformable rim 56 may then be carved according to the old upper denture curvature.

It is to be noted that, as previously mentioned, the practitioner could repeat the vertical and horizontal measurements of each tooth of the existing upper denture and transfer these measurements to the deformable rim 56. It is however believed to be within the reach of one skilled in the art to determine the position of the remaining teeth once the central incisors are accurately positioned with the help of the stone cast models of the existing dentures.

STEP 2

Measuring and Transferring the Intermaxillary Distance

The intermaxillary distance is the distance between the upper and lower jaws when the dentures are in occlusion in the mouth.

Figure 7:
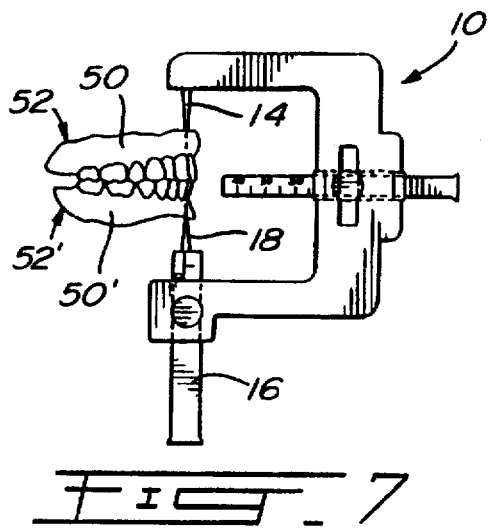
FIG. 7 illustrates a side elevational view of the dental measuring apparatus of FIG. 1 measuring, along a substantially vertical direction, existing upper and lower dentures in occlusion.

FIG. 7 illustrates the measurement of the vertical distance between the center of the upper gum ridge 50 to the center of the lower gum ridge 50' when the upper denture 52 and the lower denture 52' are in occlusion (contact). To take this measurement, the first reference point 14 is inserted in the upper denture 52 and the second reference point 18 is inserted in the lower denture 52'. The measurement between the extremity of the two reference points 14 and 18 is indicated on the first calibrated ruler 16. This measurement corresponds to the intermaxillary distance and is noted on the patient's chart.

Figure 8:
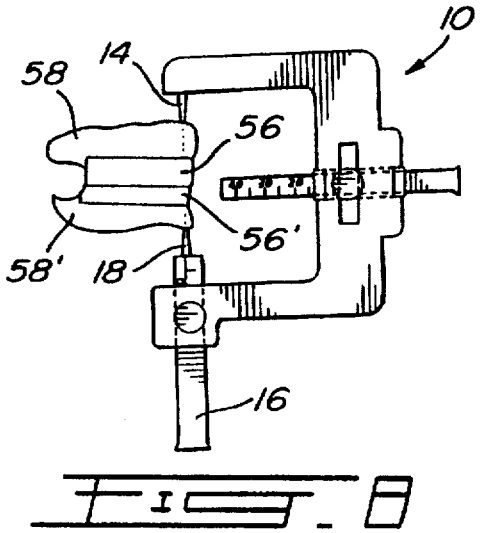
FIG. 8 illustrates a side elevational view of the dental measuring apparatus of FIG. 1 transferring measurements along a substantially vertical direction of existing upper and lower dentures in occlusion to a rim of deformable material mounted to a base-plate.

FIG. 8 of the appended drawings illustrates the transfer of the intermaxillary distance to the deformable rims 56 and 56'. The practitioner places the base-plate 58 so that the first reference point 14 is inserted in the center front of the lowest part of the base-plate 58 and places the base-plate 58' so that the second reference point 18 is inserted in the center front of the highest part of the base-plate 58'. The vertical distance from the lowest part of the inside of the base-plate 58 to the highest part of the inside of the base-plate 58' may then be measured by placing the upper deformable rim 56 and the lower deformable rim 56' in occlusion. This measurement is indicated on the first calibrated ruler 16.

The practitioner then determines the quantity of material in excess from the deformable rim 56' by performing a substraction and traces a line on the deformable rim 56' so as to obtain the desired intermaxillary distance. However, he does not trim the excess of material from the deformable rim. The practitioner inserts the upper and lower base-plates 58, 58' in the patient's mouth with the deformable rim 56' of the lower base-plate 58' previously heat softened. Then, he makes the patient close on these base-plates to the predetermined and traced line, effectively making a bite registration.

Optionally, the practitioner may measure the lower incisors' position. It is to be noted that this step is not always necessary since the upper and lower denture stone models are already made.

The measurement and the transfer of the lower incisors' position are done in the same manner as the measurement and the transfer of the upper incisors' position described hereinabove. However, as previously mentioned, it is usually not necessary to perform these measurements since the position of the lower teeth can be determined in the laboratory by comparison with the two stone denture models in occlusion.

The dental measuring apparatus of the present invention presents the following advantages:

- the measurements can be done quickly, in the clinic of the practitioner;
- the patient does not have to leave his dentures to the practitioner to get the duplication made;
- the stress associated with conventional measurements is decreased;
- the guess work is eliminated; and
- the accuracy of the measurements of the new dentures is increased.

Although the present invention has been described hereinabove by way of preferred embodiments thereof, it can be modified, without departing from the spirit and nature of the subject invention as defined in the appended claims.

What is claimed is:

1. A dental measuring apparatus for measuring existing dentures comprising:

a substantially C-shaped body including a first arm, a second arm and an intermediate part defining a longitudinal axis;

a first reference member mounted to said first arm; said first reference member projecting in a direction substantially parallel to said longitudinal axis and towards said second arm;

first ruler means mounted to said second arm; said first ruler means being slidable in a direction substantially colinear with said first reference member;

connecting means mounted to said intermediate part; said connecting means being slidable along said longitudinal axis; and second ruler means mounted to said connecting means; said second ruler means being slidable in a direction substantially perpendicular to said longitudinal axis;

whereby, by placing said existing dentures between said first reference member and said first ruler means, measurements of an existing denture in a direction parallel to said longitudinal axis may be determined from said first ruler means and, by sliding said second ruler means towards said denture, measurements of said existing denture in a direction perpendicular to said longitudinal axis may be determined from said second ruler means.

2. A dental measuring apparatus as defined in claim 1, wherein said connecting means include a sleeve element.

3. A dental measuring apparatus as defined in claim 2, wherein said connecting means further include a locking mechanism mounted to said sleeve element, said locking mechanism being adapted to positively and releasably prevent said sliding movements of said connecting means along said longitudinal axis.

4. A dental measuring apparatus as defined in claim 3, wherein said intermediate part includes a longitudinal aperture and wherein said locking mechanism of said connecting means includes
  (a) a protrusion mounted to said sleeve element and adapted to slide in said longitudinal aperture, and
  (b) a fastening means releasably mounted to said protrusion to selectively prevent said sliding of said protrusion in said longitudinal aperture.

5. A dental measuring apparatus as defined in claim 1, wherein said first ruler means include a second reference member substantially colinear with said first reference member.

6. A dental measuring apparatus as defined in claim 1, wherein said second arm further includes a locking mechanism to releasably and positively prevent said sliding movements of said first ruler means in said direction colinear with said first reference member.

7. A dental measuring apparatus as defined in claim 5, further including a plate member removably mountable to said second reference member to provide support to said existing dentures being measured.

8. A dental measuring apparatus as defined in claim 1, further including a plate member removably mountable to said first ruler means to provide support to said existing dentures being measured.

* * * * *